United States Patent [19]
Teller

[11] Patent Number: 6,094,470
[45] Date of Patent: Jul. 25, 2000

[54] METHOD OF DETERMINING THE DENSITY PROFILE

[75] Inventor: Steen Teller, Birkerød, Denmark

[73] Assignee: Wesser & Dueholm, Copenhagen K, Denmark

[21] Appl. No.: 09/125,294

[22] PCT Filed: Feb. 14, 1997

[86] PCT No.: PCT/DK97/00070

§ 371 Date: Sep. 2, 1998

§ 102(e) Date: Sep. 2, 1998

[87] PCT Pub. No.: WO97/30336

PCT Pub. Date: Aug. 21, 1997

[30] Foreign Application Priority Data

Feb. 14, 1996 [DK] Denmark ................................ 0151/96

[51] Int. Cl.[7] ................................................ G01B 15/02
[52] U.S. Cl. ................................ 378/54; 378/86; 378/87; 378/89
[58] Field of Search ............................ 378/54, 86, 87, 378/89

[56] References Cited

U.S. PATENT DOCUMENTS

| | | | |
|---|---|---|---|
| 4,123,654 | 10/1978 | Reiss et al. | 250/272 |
| 4,228,351 | 10/1980 | Snow et al. | 250/273 |
| 4,380,817 | 4/1983 | Harding et al. | 378/87 |
| 5,313,511 | 5/1994 | Annis et al. | 378/87 |
| 5,970,116 | 10/1999 | Ducholm et al. | 378/54 |

FOREIGN PATENT DOCUMENTS

0723/94  6/1994  Denmark .

WO95/35491  12/1995  WIPO .

OTHER PUBLICATIONS

Nuclear Instruments and Methods . . . , T. Pitkanen et al, "The Characterisation of Multiple Scattering . . . ", pp. 384–390, 1987.

*Primary Examiner*—David P. Porta
*Assistant Examiner*—Pamela R. Hobden
*Attorney, Agent, or Firm*—Jacobson, Price, Holman & Stern, PLLC

[57] ABSTRACT

A method of determining the density profile of a plate-shaped material M, the density of which varies discretely or continuously across the plate thickness, whereas the density at a specific depth of the plate M is preferably assumed to be constant. The inventive method employs X-rays or γ-rays from a source K. The latter source K is placed on one side of the plate M, whereas at least two detectors T, F are arranged on the opposite side of the endless plate being advanced during the measuring in the longitudinal direction. A first detector T is preferably placed in the radiating direction of the source and measures the transmittent radiation through the plate M, and the second detector F is placed outside the radiating direction of the source K and measures the scattered radiation on partial volumes along the radiating direction of the source. Based on the signals measured by the detectors it is possible to measure the density in each individual partial volume. According to the invention a compensation has furthermore been carried out for multiple scattered radiation by the measured radiation being deducted from the multiple scattered radiation.

8 Claims, 3 Drawing Sheets

METHOD OF DETERMINING THE DENSITY PROFILE

TECHNICAL FIELD

The invention relates to a method of determining the density profile of a plate-shaped material.

BACKGROUND ART

Danish Patent Application No. 0723/94 discloses a method of determining the density profile of plate-shaped materials by way of a measuring of Compton-scattered radiation from small partial volumes in the material. During the measuring, a predetermined angular relation is maintained between the incident and the scattered radiation, and the scattered radiation is adjusted by a simultaneous measuring of the incident radiation intensity and the attenuation in the entire plate-shaped material. However, such a measuring method only makes allowance for singly scattered radiation.

It is known from the article "The characterisation of multiple scattering in Compton profile measurements" by T. Pitkanen in Nuclear Instruments and Methods i Physics Research A257 (1987) pp 384–390 that multiple scattered radiation is rather important in connection with relatively thick plates.

BRIEF DESCRIPTION OF THE INVENTION

The object of the invention is therefore to provide a method of determining the density profile of a plate-shaped material, said method being more accurate than hitherto known.

A method of the above type is according to the invention characterized by compensating for multiple scattered radiation in each partial volume. The resulting measuring method is far more accurate than hitherto known, especially in connection with relatively thick plates.

According to a particularly advantageous embodiment, the multiple scattered radiation is compensated for by said radiation being reduced by the measured radiation, as the multiple scattered radiation can be found on the basis of some parameter values provided by way of a calibration measur- ing.

BRIEF DESCRIPTION OF THE DRAWING

The invention is explained in greater detail below with reference to the accompanying drawing, in which.

BEST MODE FOR CARRYING OUT THE INVENTION

Figure 1:
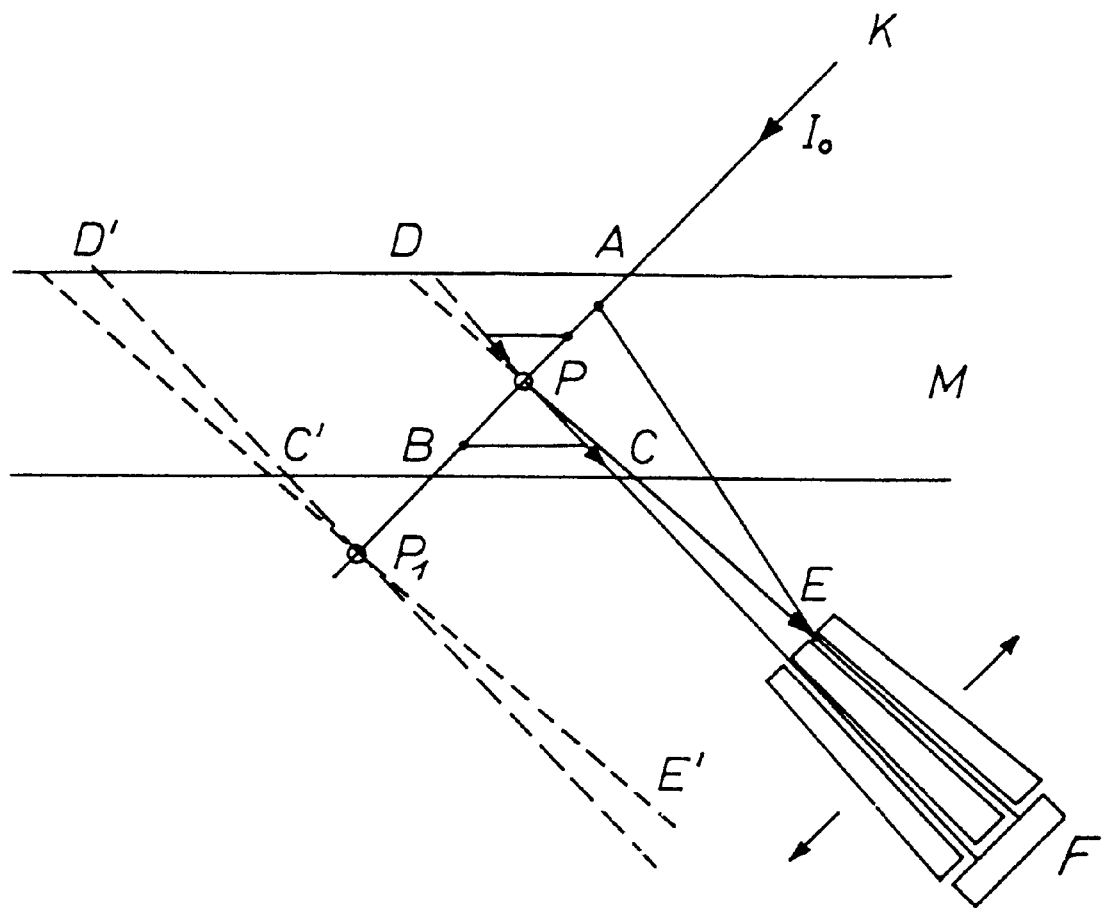
FIG. 1 illustrates how the measured intensity of the scattered radiation is composed of several values.

FIG. 1 shows how the measured intensity of the scattered radiation is composed of contributions from the considered partial volume at P and contributions from multiple scattered radiation either in the plate-shaped material M itself, where scattered radiation from the entire length AB can cause a renewed scattering from the length CD in a direction towards the detector F, or via a collimator where scattered radiation from the length AB meets the wall of said collimator and is scattered towards the detector F.

The intensity of the multiple scattered radiation is not correlated with the density of the partial volume at P, but almost unambiguously correlated with the surface weight $\rho$ of the plate-shaped material M, where $\rho$ is the average density and t is the thickness.

The latter has been confirmed by simulation calculations performed by the known Monte-Carlo-method. For the present measuring geometry with a narrow incident beam and a strong collimation in front of the detector for scattered radiation and an optical thickness of $\mu \cdot \rho p \cdot t \leq 1$, where $\mu$ is the absorption coefficient, the intensity of multiple scattered radiation $I_{MS}$ can be approximately expressed by $$I_{MS} = \beta I_0 \mu \cdot \rho \cdot t (1 - \alpha \mu \rho t) \tag{1}$$

where $I_0$ is the incident intensity.
$I_{MS}$ is proportional to the intensity $I_0$ of incident radiation, and the parameters $\alpha$ and $\beta$ depend on the actual measuring geometry (the extent of the beam, the visual field of and the distance to the collimator and the detector etc. Furthermore, $\beta$ depends on the position of P of the actual partial volume, from which singly scattered radiation is to be measured. When the location $P_1$ is considered outside the plate M, a definite probability applies of multiple scattered radiation over the length AB through C', D' or E' to the staggered detector. $I_{MS}$ decreases, however, proportional to an increasing distance to C', D' from AB.

The above observations result in a possibility of compensating for multiple scattered radiation in the following manner.

Figure 2:
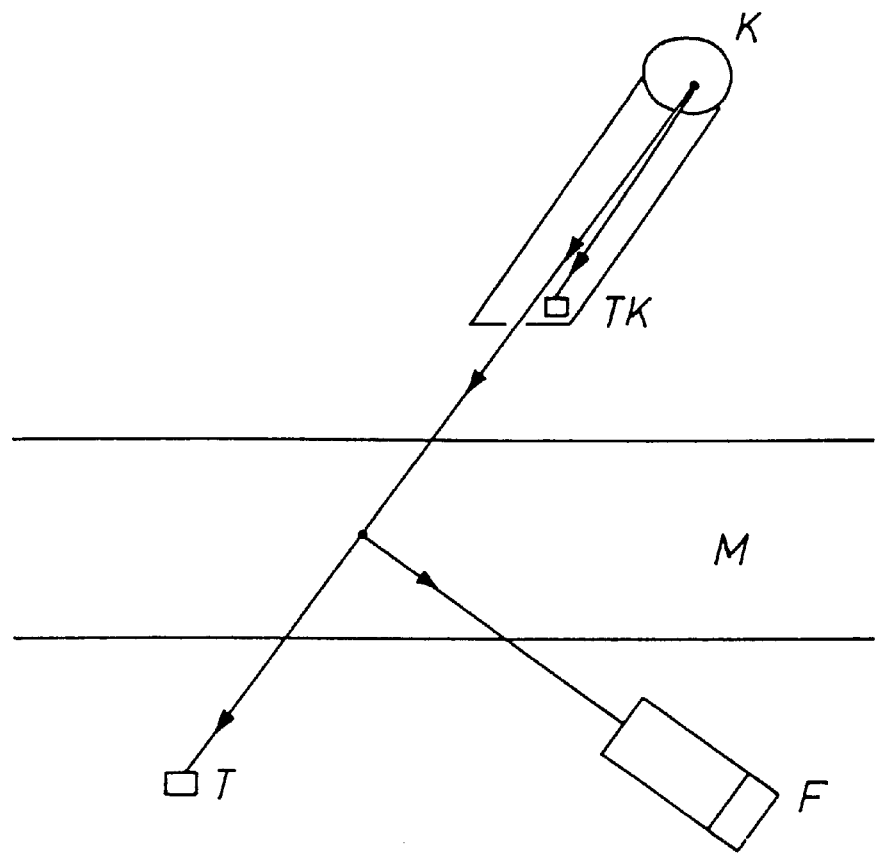
FIG. 2 shows a measuring arrangement wherein an additional detector is coupled between the X-ray source and the plate-shaped material.

As shown in FIG. 2, a detector TK is placed between the X-ray source K and the plate-shaped material M. The detector TK measures the time-related variation of the intensity of the source K. Together, the measuring signal from the detector TK and the transmitted measuring signal T provide the relation $$e^{-\mu \rho t} = \frac{TK}{T} \quad \text{eller} \quad \mu \cdot \rho \cdot t = \ln \frac{TK}{T}$$

where $\mu$ is the absorption coefficient, $\rho$ is the density, and t is the thickness, whereafter the adjusted density $\rho_{korr}$ is found for a partial volume at P according to Danish patent application No. 0723/94 by a deduction of $I_{MS}(P)$ as $$\rho_{korr}(P) = C \cdot \frac{I_{FS}(P) - I_{MS}(P)}{T} \tag{2}$$

$$= c \cdot \left( \frac{I_{FS}(P)}{T} - \frac{TK}{T} \cdot \beta(P) \cdot \ln \frac{TK}{T} \left( 1 - \alpha \cdot \ln \frac{TK}{T} \right) \right)$$

where $T = I_0 e^{-\mu \rho t}$ or $TK = I_0 \cdot k$ (k=constant fraction of the intensity of the X-ray tube measured as $I_0$ at T for an empty measuring gap) has been adjusted by the factor k.

Figure 3:
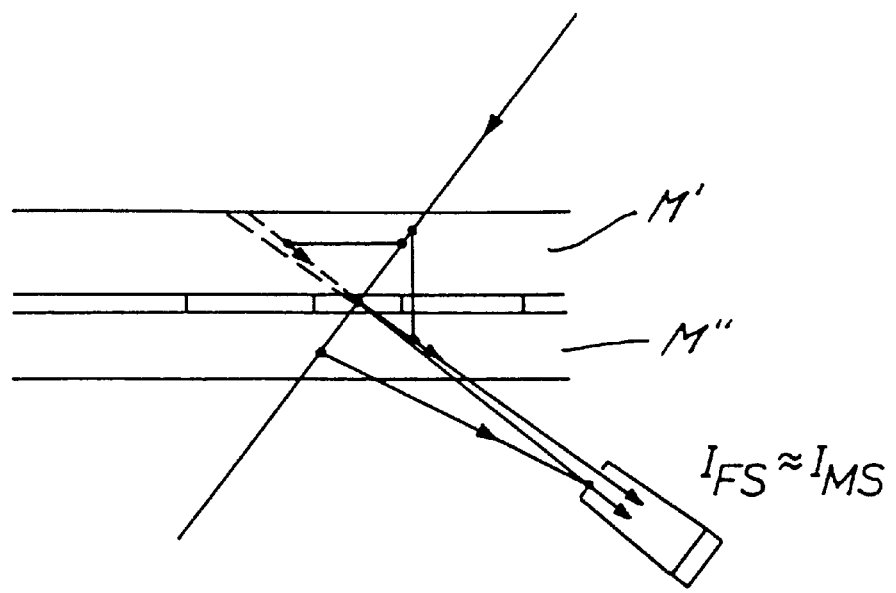
FIG. 3 shows an arrangement of two plate-shaped materials arranged at a mutual distance.
Figure 4:
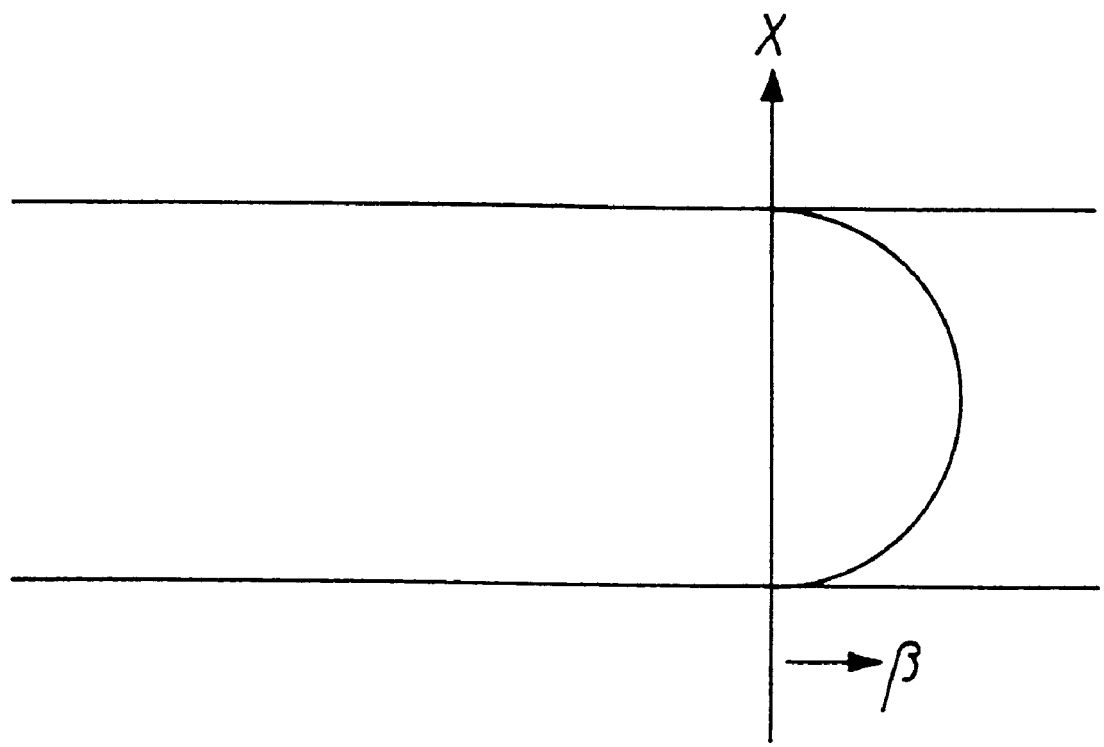
FIG. 4 shows an example of how one of the parameter values β varies versus the height of the plate material.

The parameters $\alpha$, $\beta$ are determined by way of a calibration measuring for the actual measuring arrangement. In FIG. 3 two plates M', M" are interspaced a distance corresponding to the length of approximately three partial volumes. When $I_{FS}$ is measured from the resulting air gap between the plates M', M", only multiple scattered radiation is measured. The measuring of $I_{FS}$ is repeated with another set of plates (larger/smaller thickness and/or higher/lower density), which results in two equations with two unknown quantities for determining α and β. The variation of β with P relative to the central value is subsequently determined by means of a set of plates of thicknesses corresponding to 3–4 partial volumes, between which an air gap is established at various depths.

As the effect of multiple scattered radiation is vague (approximately 10% corresponding to the value of α) of singly scattered radiation measured in a typical measuring object of a density of approximately 1 g/cm$^3$), it is sufficient to know the absolute contribution at the centre of the plate-shaped material. Subsequently the relative variation of β from the lower edge to the upper edge measured for one thickness can be utilized for calculating the multiple scattering contribution across plates of an arbitrary thickness.

In practice, the density profile measuring device is supplemented with an optical thickness meter, such as an optical reflection meter, whereby both the size $$\mu \cdot \rho \cdot t = \ln\frac{TK}{T}$$

as the thickness t are found in a computer at the beginning of the production and are continuously updated. Based on the thickness t the position of the detector F is calculated, said position corresponding to "0", "½ t" and "t". As far as the central position corresponding to ½ t is concerned, the values of α and β are taken from a table. A function β(P) renders it possible to calculate the relative variation of β across the measured thickness, whereafter the measured scattering densities are adjusted by means of formula (2).

The selection of angle of incidence and scattering angle as well as the utilization of the signals from the three detectors follow the method according to Danish patent application No. 0723/94.

A γ-ray source may be used instead of an X-ray source.

What is claimed is:

1. A method of determining the density profile of a plate-shaped material (M), the density of which varies discretely or continuously across the plate thickness, whereas the density at a specific depth of said plate is preferably assumed to be constant, by means of X-rays or γ-rays from a source (K) being arranged on one side of said plate (M), whereby at least two detectors (T, F) are arranged on the opposite side of the plate being advanced during measuring in the longitudinal direction, one first detector (T) preferably being placed in the radiating direction of the source (K) so as to measure the radiation transmitted through the plate (M), and at least one detector (F) being placed outside the radiation direction of said source (K) so as to measure the radiation scattered from partial volumes along the radiating direction of the source (K), wherein multiple scattered radiation in each individual partial volume is compensated for by subtracting the multiple scattered radiation from the measured radiation, said multiple scattered radiation being calculated by means of the formula $$I_{MS}=\beta I_0\mu\cdot\rho\cdot t(1-\alpha\cdot\mu\rho t)$$

where $I_0$ represents incident intensity, and α and β depend on measuring arrangement, and wherein a relative variation of β is determined by means of a number of sets of plates of thicknesses corresponding to a number of partial volumes, an air gap being established between said plates at various depths.

2. The method as claimed in claim 1, wherein calibration is achieved by means of at least two sets of plates with a gap between the plates for determining α and β from two equations containing α and β.

3. A method for determining a density profile of a plate (M), the density of which varies across a thickness of said plate, by means of radiation from a source arranged on one side of said plate, with at least two detectors being arranged on a side of said plate opposite from said source, a first detector being placed in a radiating direction of the radiation source so as to measure radiation transmitted through said plate (M), and a second detector being placed outside the radiation direction of said radiation source so as to measure radiation scattered from partial volumes along the radiating direction of said source, wherein multiple scattered radiation in each individual partial volume is compensated for by subtracting the multiple scattered radiation from the measured radiation, said multiple scattered radiation being calculated by means of a formula $$I_{MS}=\beta I_0\mu\cdot\rho\cdot t(1-\alpha\cdot\mu\rho t)$$

where $I_0$ represents incident intensity, and α and β depend on measuring arrangement, and wherein a relative variation of β is determined by means of a number of sets of plates of thicknesses corresponding to a number of partial volumes, an air gap being established between said plates at various depths.

4. The method as set forth in claim 3, wherein density at a specific depth of said plate (M) is assumed to be constant.

5. The method as set forth in claim 4, wherein at least said plate (M) is wood-based.

6. The method as claimed in claim 3, wherein calibration is achieved by means of at least two sets of plates with a gap between the sets of plates for determining α and β from two equations containing α and β.

7. The method as claimed in claim 3, wherein the source of radiation is an X-ray source.

8. The method as claimed in claim 3, wherein the source of radiation is a γ-ray source.

* * * * *